(12) United States Patent
Dietz et al.

(10) Patent No.: US 6,957,164 B2
(45) Date of Patent: Oct. 18, 2005

(54) ELASTIC SENSOR MESH SYSTEM FOR 3-DIMENSIONAL MEASUREMENT, MAPPING AND KINEMATICS APPLICATIONS

(75) Inventors: Timothy Alan Dietz, Austin, TX (US); Nadeem Malik, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 16 days.

(21) Appl. No.: 10/387,763

(22) Filed: Mar. 13, 2003

(65) Prior Publication Data

US 2003/0139896 A1 Jul. 24, 2003

Related U.S. Application Data

(62) Division of application No. 09/578,741, filed on May 25, 2000, now Pat. No. 6,640,202.

(51) Int. Cl.[7] .............................................. G06F 15/00
(52) U.S. Cl. ..................... 702/155; 702/167; 702/156; 702/161; 342/118; 342/126; 342/146
(58) Field of Search ................................ 702/153, 167, 702/161, 104, 150, 94; 338/210; 600/595; 128/925; 340/524, 573.7, 619, 686.1; 342/118, 126, 146; 704/271; 379/52; 382/100

(56) References Cited

U.S. PATENT DOCUMENTS

| | | | | |
|---|---|---|---|---|
| 4,542,291 A | * | 9/1985 | Zimmerman | 250/231.1 |
| 5,280,265 A | * | 1/1994 | Kramer et al. | 338/210 |
| 5,592,401 A | * | 1/1997 | Kramer | 702/153 |
| 5,744,953 A | | 4/1998 | Hansen | 324/207.17 |
| 5,896,191 A | | 4/1999 | Beier et al. | 356/35.5 |
| 5,930,741 A | * | 7/1999 | Kramer | 702/153 |
| 6,035,398 A | | 3/2000 | Bjorn | 713/186 |
| 6,148,280 A | * | 11/2000 | Kramer | 702/153 |
| 6,640,202 B1 | * | 10/2003 | Dietz et al. | 702/167 |
| 6,809,462 B2 | * | 10/2004 | Pelrine et al. | 310/319 |
| 2002/0152077 A1 | * | 10/2002 | Patterson | 704/271 |

* cited by examiner

Primary Examiner—John Barlow
Assistant Examiner—Hien Vo
(74) Attorney, Agent, or Firm—Duke W. Yee; Mark E. McBurney; Theodore D. Fay, III (57) ABSTRACT

An apparatus, method, and system for determining the shape of a three dimensional object. In a preferred embodiment, the apparatus includes an array of sensors and elastic connections between the sensors within the array. When placed over a three dimensional object, the array of sensors deforms to conform to the surface topology of the three dimensional object. The sensors are connected to a data processor in which the data from the sensors is taken to construct a three-dimensional representation of the actual physical three dimensional object.

28 Claims, 5 Drawing Sheets

ELASTIC SENSOR MESH SYSTEM FOR 3-DIMENSIONAL MEASUREMENT, MAPPING AND KINEMATICS APPLICATIONS

This application is a divisional of application Ser. No. 09/578,741 filed May 25, 2000, now U.S. Pat. No. 6,640,202.

BACKGROUND OF THE INVENTION

1. Technical Field

The present application relates to a method, system, and apparatus for making 3-dimensional measurements of animate and inanimate objects.

2. Description of Related Art

The unique shapes and proportions of many animate and inanimate objects, especially animate ones with considerable variability in three dimensional space (e.g., the human form), make them difficult to accurately record for a variety of applications. For example, covering objects (e.g., clothing the human form), mapping movements of these objects (e.g., tracing a human form's movements in three dimensional space, say while performing a sporting activity like a golf swing), and analyzing other dimensional characteristics become quite difficult.

In the area of garment manufacturing, a system exists to acquire precise measurements of the human form for use in creating customized clothing. This system requires a very expensive room be built. The room includes multiple light beam sources. A person for whom measurements are needed enters the room and is then scanned by the multiple light beams. The data gathered through this process is used to create measurements which are used in the creation of customized clothing. However, the equipment necessary to perform this procedure is quite large and very expensive, often costing in excess of $300,000 per system.

Another existing technology utilizes electro-optical sensors in conjunction with a glove that a person wears. These devices are capable of measuring flex and movement to some degree and translating it into computer usable data. However, these devices are bulky and require different sizes for different individuals.

Therefore, a method, system, and apparatus that provides a simple and cost effective way to accurately record a wide range of sizes and shapes of such animate and inanimate objects is desirable. Such a solution would open up opportunities for customized clothing, more effective kinematics training methods and a host of other applications that today are costly and only available where there are expensive facilities or limited resources.

SUMMARY OF THE INVENTION

The present invention provides an apparatus, method, and system for determining the shape of a three dimensional object. In a preferred embodiment, the apparatus includes an array of sensors and elastic connections between the sensors within the array. When placed over a three dimensional object, the array of sensors conforms to the surface topology of the three dimensional object. The sensors are connected to a data processor in which the data received from the sensors is used to construct a three-dimensional representation of the actual physical three dimensional object.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
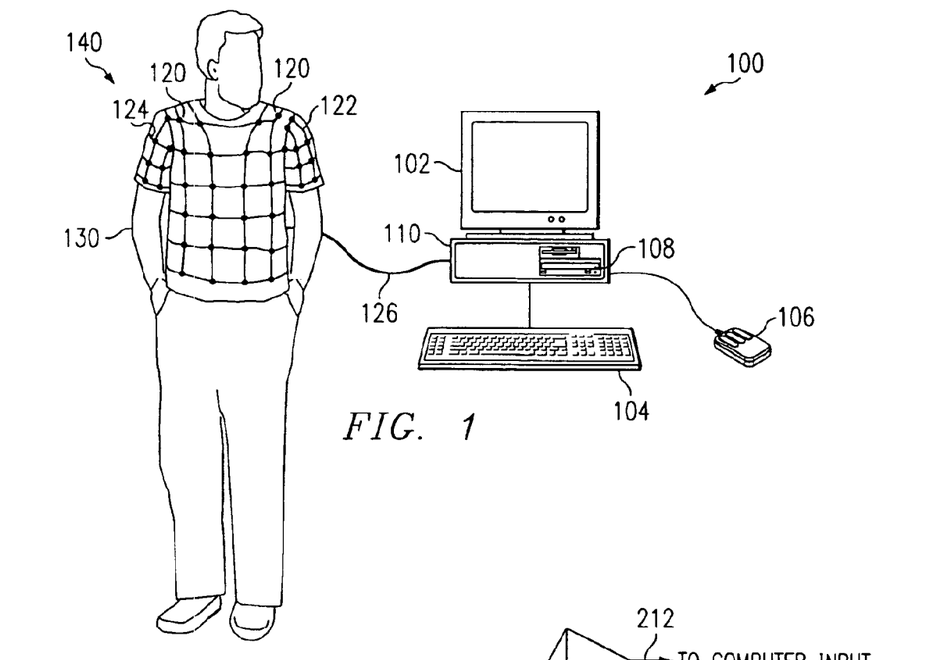
FIG. 1 depicts a pictorial representation of a data processing system and apparatus for determining the 3-dimensional structure of objects in accordance with a preferred embodiment of the present invention.

With reference now to the figures and in particular with reference to FIG. 1, a pictorial representation of a data processing system and apparatus for determining the 3-dimensional structure of objects is depicted in accordance with a preferred embodiment of the present invention. In this example, a personal computer 100 connected by a USB line 126 to an elastic sensor mesh system 140, worn by a person 130 is illustrated. This arrangement allows for the 3-dimensional measurement mapping of the person 130 is depicted.

Elastic sensor mesh 140 includes a plurality of sensors attached to nodes of the mesh sensor 140, such as node 120. Each node is connected to at least one other sensor by elastic connectors, such as, for example, elastic connectors 122 and 124. Elastic sensor mesh 140 initially has a known baseline shape (i.e., the distances and angles between neighboring sensors are known). When elastic sensor mesh 140 is placed over a three-dimensional object, such as, for example the person 130 depicted in FIG. 1, the plurality of elastic connectors expand away from the baseline shape sufficiently to conform to the shape and size of the object for which modeling of the three dimensional shape is desired. The elastic sensor mesh 140 should be somewhat smaller than the object for which the three dimensional shape is desired such that after expansion of the elastic connectors, the elastic sensor mesh 140 fits snugly around the mapped object. Any loose areas in elastic sensor mesh 140 will result in a distorted generation of the picture of the object such that a true representation of the object cannot be obtained.

Each of the plurality of sensors, which may be located at a node, such as, for example node 120, or between a pair of nodes, collects data regarding the distance and the angle to each adjacent sensor. This information is collected and passed through USB line 126 to personal computer 100, where it is then analyzed and a 3-dimensional image of the object, in this case, the torso of person 130, is generated using any number of algorithms. Such algorithms for generating a 3-dimensional image based on the relation of a series of points to other points are well known to those of ordinary skill in the art and many of which may be found in the public domain.

Taking readings of this data, an accurate 3-dimensional mapping of the form can be done by analyzing the sensor data from the deformed mesh and comparing it with the base-line data. The amount of computing power needed to perform this function is quite modest by current standards and, as discussed above, the algorithms are well known.

In one coordinate system, the linear (X-Y) coordinates are directly available as a function of the stretch movement of each segment of elastic sensor mesh 140. The X-Y coordinates correspond to orthogonal directions on the surface of the elastic sensor mesh 140. The Z-coordinate, which is defined as a direction normal from the surface of the elastic sensor mesh 140, may be calculated by calculating the interior angle from the lengths of any two sides of the triangle that is formed at each node. The only information now missing is whether the mesh was pushed in or pushed out. However, since the mesh is always constructed such that it is, in its normal form, smaller than the object on which it is to be worn, the Z-coordinate movement is always in the outward direction. The number of sensors used within elastic sensor mesh 140 may vary according to the application. For example, for determining measurements for tailoring clothing, where fit needs to be accurate, the number of sensors per unit area may be more dense. For athletic form comparison and training, the sensors may be further apart and less dense since the objective in this application is to conform fairly gross motions and form to an ideal motion and form. One of the more densely packed sensor configurations may be for gloves, where the movements are transmitted to a computer system for virtual reality or telepresence applications.

Another application of the present invention is for use in gathering data to build custom shipping containers. The object to be shipped is measured with the elastic sensor mesh 140 at a remote location. The measurements are transmitted to a manufacturer for construction of the necessary close-fitting packing material. The packing material is then placed into an empty container and shipped to the location where the object is located, from which the object can be packed and shipped to its final destination.

With respect to collecting and analyzing data from elastic sensor mesh 140, personal computer 100 includes a system unit 110, a video display terminal 102, a keyboard 104, storage devices 108, which may include floppy drives and other types of permanent and removable storage media, and a pointing device 106, such as a mouse. Personal computer 100 also includes a USB adapter to receive data via USB wire 126. Alternatively, other data transmission devices other than USB wire 126 may be used for transferring data from elastic sensor mesh 140 to personal computer 100, such as, for example, other wire type devices and wireless communication devices. Additional input devices may be included with personal computer 100, as will be readily apparent to those of ordinary skill in the art.

The personal computer 100 can be implemented using any suitable computer. Although the depicted representation shows a personal computer, other embodiments of the present invention may be implemented in other types of data processing systems, such as for example, mainframes, workstations, network computers, laptop computers, and palm computers. Computer 100 also preferably includes a graphical user interface that may be implemented by means of systems software residing in computer readable media in operation within computer 100.

Although elastic sensor mesh 140 has been depicted as having a USB connection to computer 100, other means of transferring the information gathered by elastic sensor mesh 140 to computer 100 may be used as well. For example, USB line 126 may be a fire-wire connection from a central collection device built into the webbing of elastic sensor mesh 140. Alternatively, the data may be transferred to computer 100 using a wireless communication mechanisms, such as, for example, the 900 MHz communication standard utilized by cordless telephones. The method of transmitting the information from the elastic sensor mesh 140 to the computer 100 depends on the application and the amount of mobility required.

It should be noted that while the present invention has been described with reference to mapping the 3-dimensional shape of a human torso, the present invention is not limited to such. The present invention may be utilized to map the 3-dimensional shape of other animate or inanimate objects. The elastic sensor mesh may be tailored to match the general shape for which the 3-dimensional shape is desired to be mapped. For example, the elastic sensor mesh may be tailored to resemble a shirt in order to map the 3-dimensional shape of a human torso or to a generic shape (e.g., a tube with small diameter and great elasticity) for mapping the 3-dimensional shape of non-specific objects.

Figure 2:
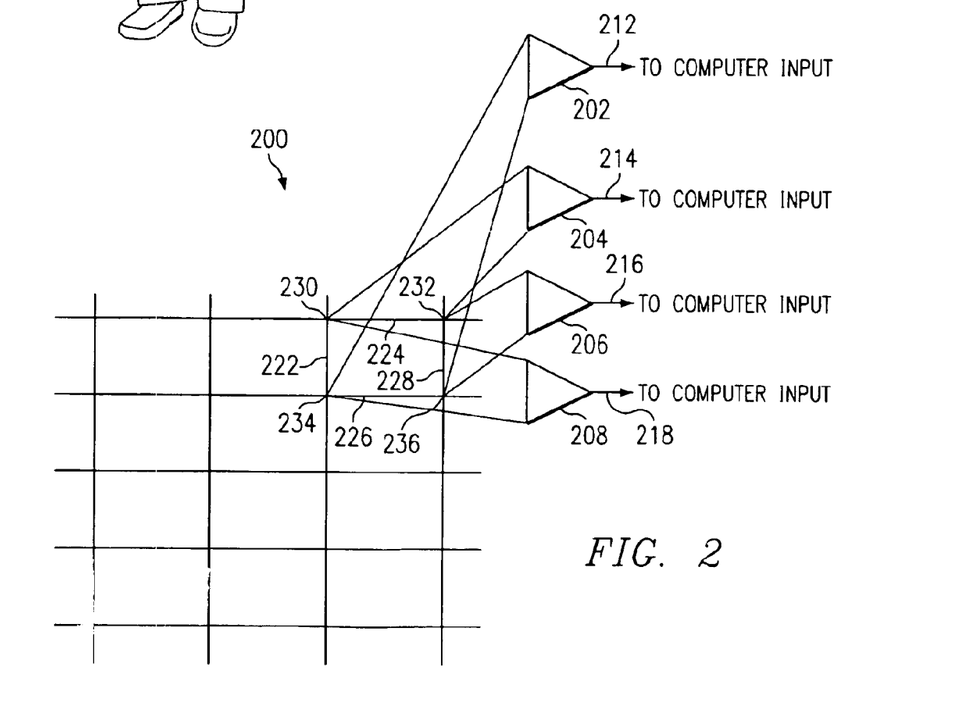
FIG. 2 depicts a block diagram of an apparatus for determining the shape of a 3-dimensional object in accordance with the present invention.

With reference now to FIG. 2, a block diagram of a elastic sensor mesh apparatus for determining the shape of a 3-dimensional object is depicted in accordance with the present invention. Elastic sensor mesh 200 is an example of an elastic sensor mesh, such as, for example, elastic sensor mesh 140 in FIG. 1. Elastic sensor mesh 200 is made up of elastic wire segments, such as, elastic wire segments 222–228. Each of elastic wire segments 222–228 comprises elastic wire of the kind used in strain gauges. A strain gauge wire provides increasing resistance to voltage as it is stretched. Alternatively, the strain gauge may be incorporated within the individual sensors to measure strain in the connections to the other segments.

Each pair of nodes 230–236 at each end of elastic wire segments 222–228 is connected to one of comparator operation amplifiers (op-amps) 202–208. For example, comparator op-amp 202 is connected to node 234 and to node 236 such that the change in voltage across elastic wire segment 226 may be determined. Each of comparators 202–208 sends an output signal alone signal lines 212–218 to an analog-to-digital converter (ADC) input of the computer. The output signal is the change in voltage across the two monitored points, such as nodes 234 and 236, as the segment, such as segment 226, stretches from its normal position. Based on similar inputs from each of the segments and the identifications (IDs) of the comparators 202–208 involved, the computer calculates the 3-dimensional movement of the mesh 200 from its known; normal baseline configuration.

Elastic sensor mesh 200 is given as an example of a elastic sensor mesh and is not intended as an architectural limitation of the present invention. Many other types of sensors may be used and perform equally as well as that presented herein. The basic requirement of a sensor is that the sensor is able to sense the distance and angle to the adjacent sensors. The accuracy and density of sensors is dependent upon the type of application for which the mesh sensor is to be used.

Figure 3:
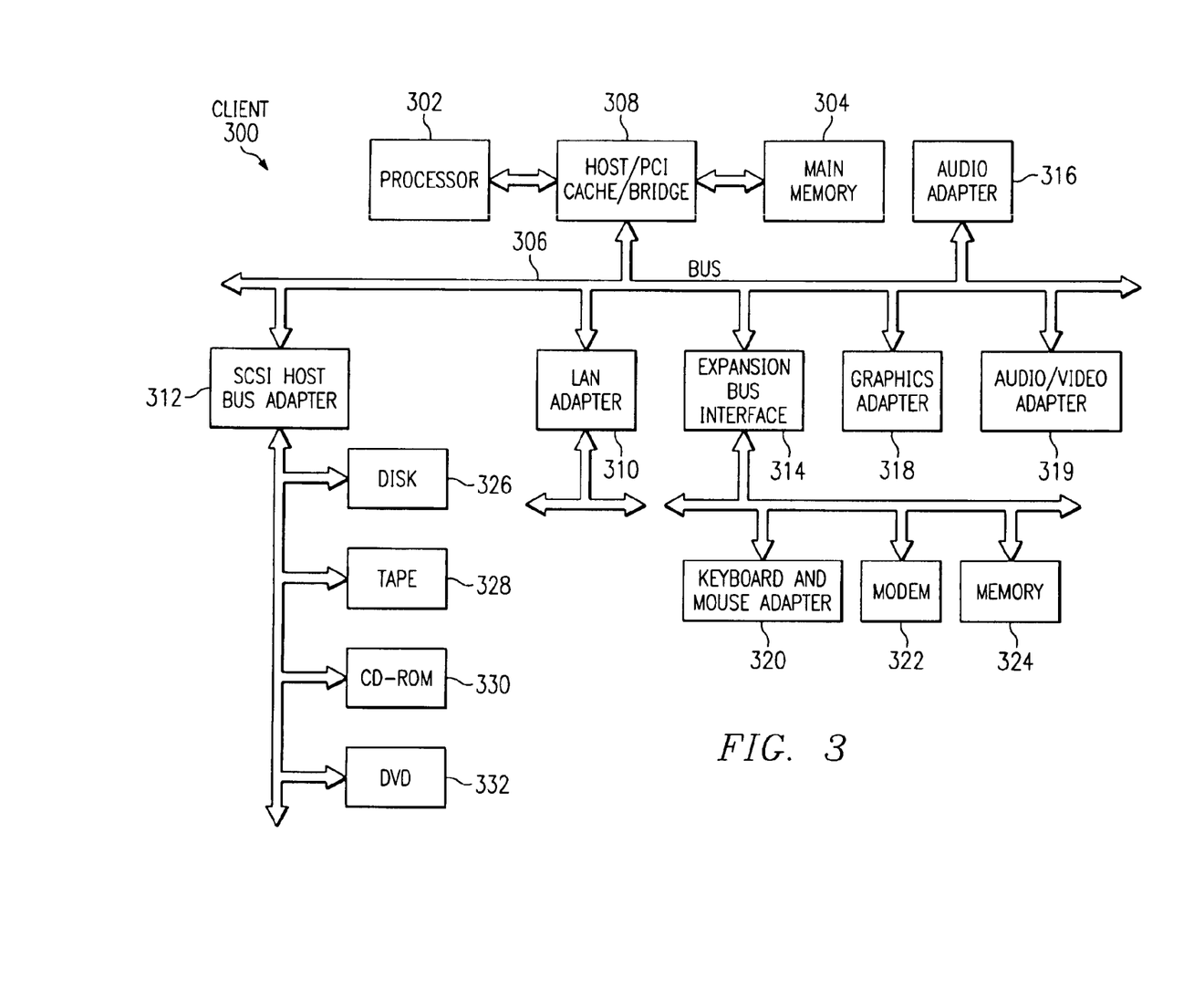
FIG. 3 depicts a block diagram of a data processing system in which some of the processes of the present invention may be implemented.

With reference now to FIG. 3, a block diagram of a data processing system in which some of the processes of the present invention may be implemented is illustrated. Data processing system 300 is an example of a computer, such as computer 100 in FIG. 1, in which data taken from a 3-dimensional measuring device can be processed. Data processing system 300 employs a peripheral component interconnect (PCI) local bus architecture. Although the depicted example employs a PCI bus, other bus architectures, such as Micro Channel and ISA, may be used. Processor 302 and main memory 304 are connected to PCI local bus 306 through PCI bridge 308. PCI bridge 308 may also include an integrated memory controller and cache memory for processor 302. Additional connections to PCI local bus 306 may be made through direct component interconnection or through add-in boards. In the depicted example, local area network (LAN) adapter 310, SCSI host bus adapter 312, and expansion bus interface 314 are connected to PCI local bus 306 by direct component connection. In contrast, audio adapter 316, graphics adapter 318, and audio/video adapter (A/V) 319 are connected to PCI local bus 306 by add-in boards inserted into expansion slots. Expansion bus interface 314 provides a connection for a keyboard and mouse adapter 320, modem 322, and USB interface 324 for receiving the position data of nodes within an elastic sensor mesh, such as, for example, elastic sensor mesh 140 in FIG. 1.

In the depicted example, SCSI host bus adapter 312 provides a connection for hard disk drive 326, tape drive 328, CD-ROM drive 330, and digital video disc read only memory drive (DVD-ROM) 332. Typical PCI local bus implementations will support three or four PCI expansion slots or add-in connectors.

An operating system runs on processor 302 and is used to coordinate and provide control of various components within data processing system 300 in FIG. 3. The operating system may be a commercially available operating system, such as OS/2, which is available from International Business Machines Corporation. "OS/2" is a trademark of International Business Machines Corporation. An object oriented programming system, such as Java, may run in conjunction with the operating system, providing calls to the operating system from Java programs or applications executing on data processing system 300. Instructions for the operating system, the object-oriented operating system, and applications or programs are located on a storage device, such as hard disk drive 326, and may be loaded into main memory 304 for execution by processor 302.

Those of ordinary skill in the art will appreciate that the hardware in FIG. 3 may vary depending on the implementation. For example, other peripheral devices, such as optical disk drives and the like, may be used in addition to or in place of the hardware depicted in FIG. 3. Furthermore, other devices, such as, for example, a wireless communications interface, may be used in place of USB 324 for receiving data from elastic sensor mesh 140. The depicted example is not meant to imply architectural limitations with respect to the present invention. For example, the processes of the present invention may be applied to multiprocessor data processing systems.

Figure 4:
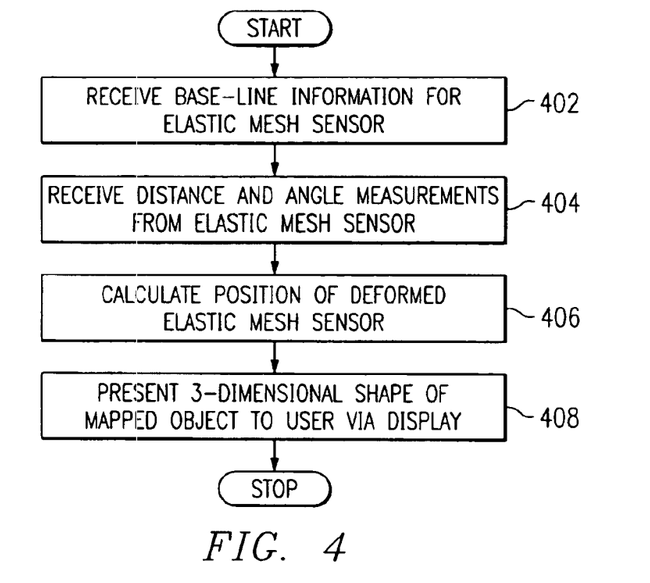
FIG. 4 depicts a flowchart illustrating a method of receiving data from an elastic sensor mesh and constructing and 3-dimensional image from that data in accordance with the present invention.

With reference now to FIG. 4, a flowchart illustrating a method of receiving data from an elastic sensor mesh and constructing and 3-dimensional image from that data is depicted in accordance with the present invention. The process illustrated in FIG. 4 may be performed on a data processing system, such as, for example, data processing system 300 in FIG. 3, which may be used in conjunction with an elastic sensor mesh, such as elastic sensor mesh 200 in FIG. 2.

To begin, the computer receives base-line information for the elastic sensor mesh being utilized (step 402). This base-line information identifies the beginning normal shape of the elastic sensor mesh, which is needed in order to determine the displaced shape of the sensor after deformation around a 3-dimensional object. This base-line information may be transmitted by the elastic sensor to the computer or may be input by a user.

Next, the computer receives distance and angle measurements from the elastic sensor mesh (step 404). The distance and angle measurements indicate the distance and angle by which neighboring nodes of the mesh have been separated as a result of the distortion of the elastic sensor mesh being placed around a 3-dimensional object. The computer then calculates the position of each node in the deformed elastic mesh from which a 3-dimensional representation may be generated (step 406). The generated 3-dimensional image of the mapped object is then presented to a user via a display (step 408). The image presented to the user is actually a 2-dimensional simulation of the 3-dimensional object, but with appropriate shading or other indication to indicate the 3-dimensional character of the object. Furthermore, the image presented to the user may be manipulated to present differing views to the user. Also, other images may be overlaid with the image of the 3-dimensional object mapped, such that the two images may be compared.

Figure 5A:
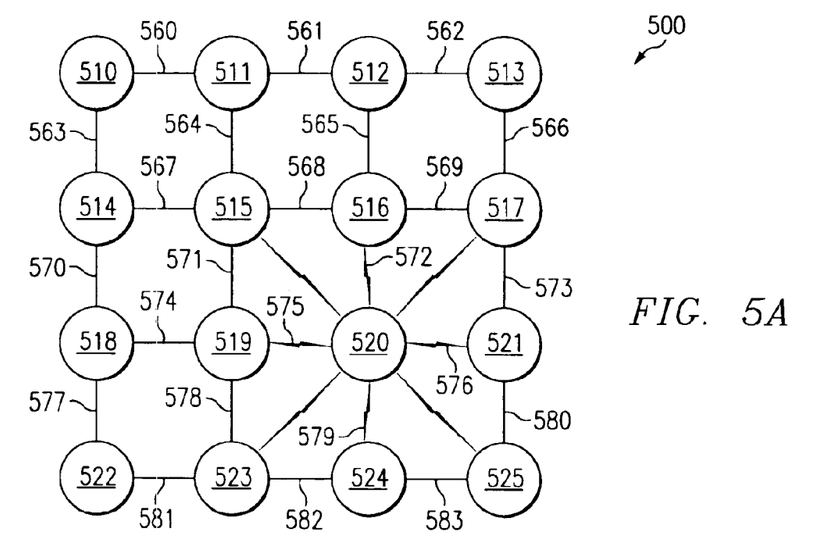
FIGS. 5A–5B depict schematic diagrams of an alternate embodiment of an elastic sensor mesh configuration in accordance with the present invention.
Figure 5B:
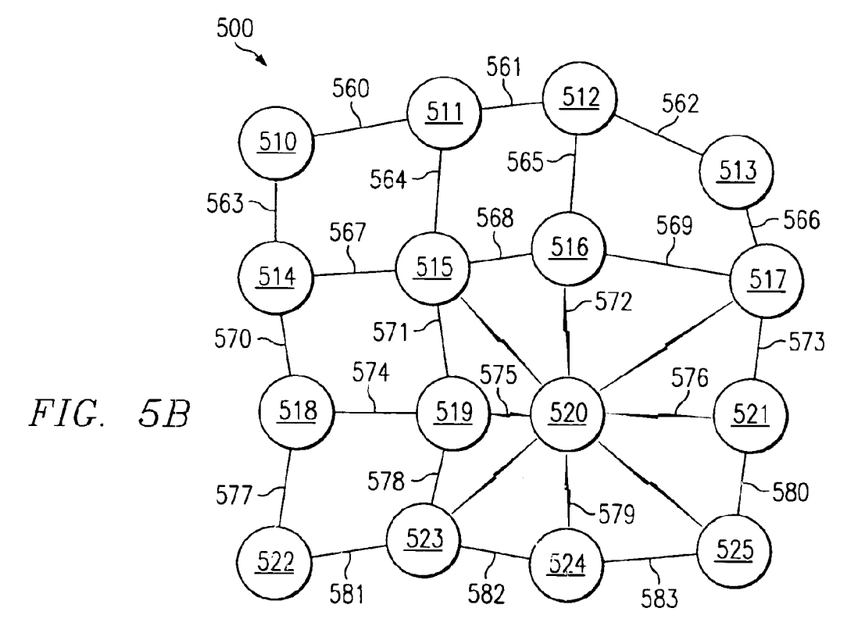

With reference now to FIGS. 5A–5B, schematic diagrams of an alternate embodiment of an elastic sensor mesh configuration are depicted in accordance with the present invention. FIG. 5A depicts elastic sensor mesh 500 in an undeformed state, while FIG. 5B depicts elastic sensor mesh 500 after deformation around a 3-dimensional object. In this embodiment, elastic sensor mesh 500 includes a number of sensors 510–525 each connected to other sensors 510–525 within elastic sensor mesh 500 by elastic connections 560–583. Each of sensors 510–525 emits radio frequency (RF) signals indicating its identity. Each of the sensors 510–525 receives the RF signals from neighboring ones of sensors 510–525 and, using signal strength, sensor identity, and the known initial separation of the sensors 510–525, calculates a relative position. One of the sensors 510–525 may arbitrarily be assigned as the (0, 0, 0) point as a reference for all other sensors 510–525. The relative position of each of sensors 510–525 is then sent to a computer (not shown) for display and manipulation. The known initial separation may be programmed into each of sensors 510–525 or may be determined by each sensor prior to deformation around a 3-dimensional object using the signal strength and sensor identity for each signal received.

Figure 6:
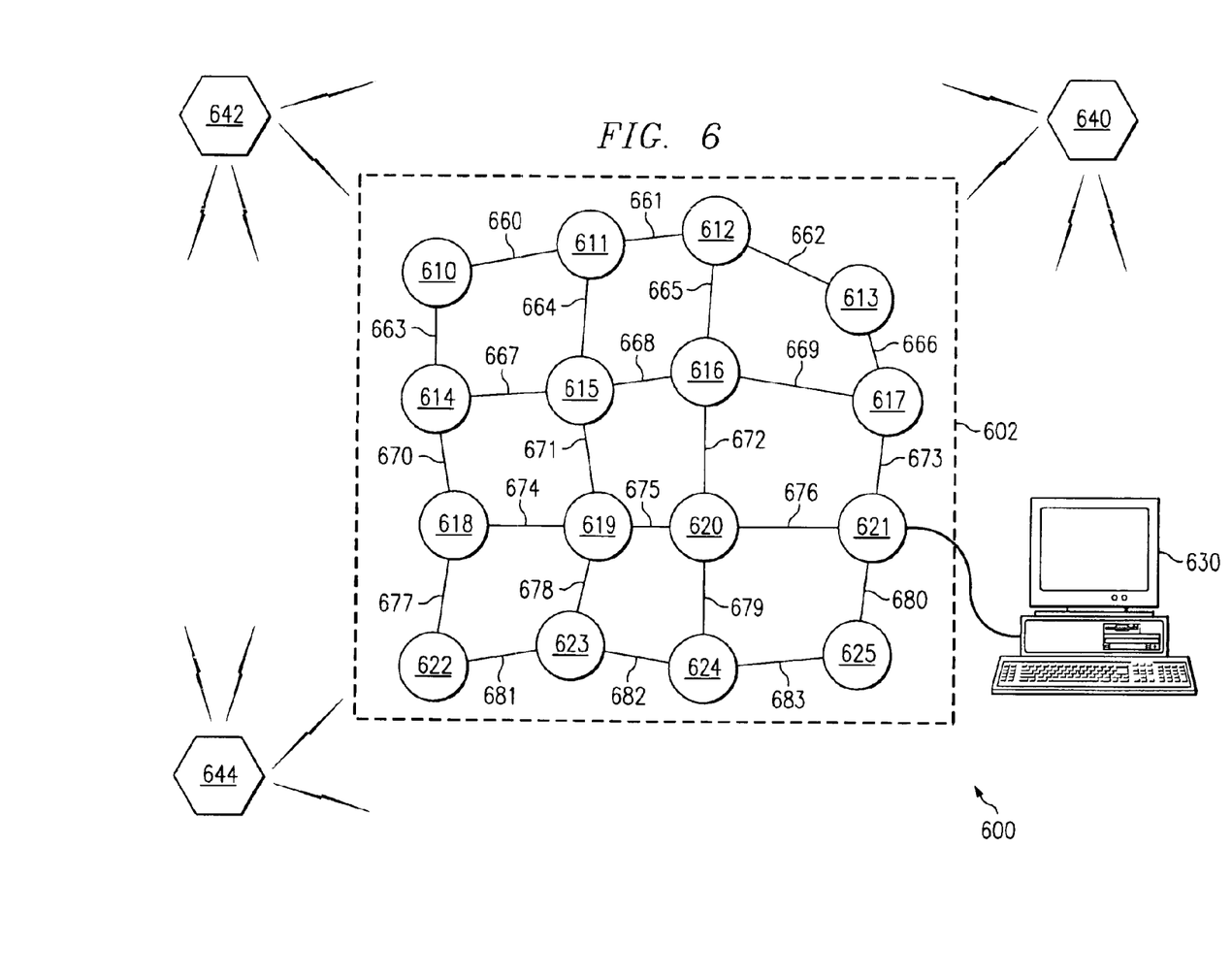
FIG. 6 depicts a schematic diagram of another alternate embodiment of an elastic sensor mesh system for mapping the 3-dimensional shapes of objects in accordance with the present invention.

With reference now to FIG. 6, a schematic diagram of another alternate embodiment of an elastic sensor mesh system for mapping the 3-dimensional shapes of objects is depicted in accordance with the present invention. In this embodiment, elastic sensor mesh system 600 includes an elastic sensor mesh 602, three fixed RF sources 640–644, and computer 630. Elastic sensor mesh 602 includes a plurality of sensors 610–625 each connected to others of sensors 610–625 by elastic connections 660–683. Each sensor calculates its relative position to fixed radio frequency sources 640–644 by receiving RF signals from each of radio frequency sources 640–644 and triangulating its position. The position of each of sensors 610–625 is then sent to computer 630 for display and manipulation.

Figure 7:
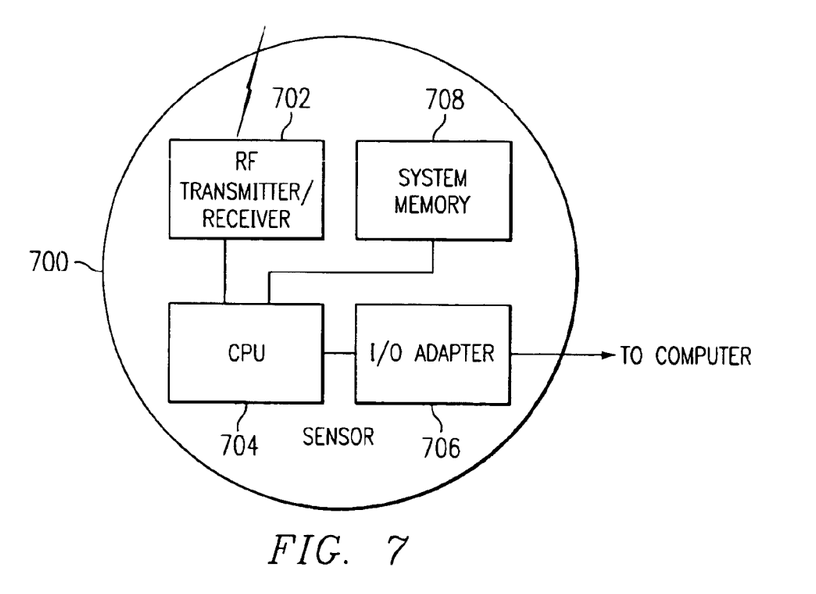
FIG. 7 depicts a block diagram of a sensor for use in an elastic sensor mesh system in accordance with the present invention.

With reference now to FIG. 7, a block diagram of a sensor for use in an elastic sensor mesh system is depicted in accordance with the present invention. Sensor 700 is an example of a sensor that may be used for determining its position relative to other sensors within an elastic sensor mesh, such as, for example, elastic sensor mesh 500 depicted in FIGS. 5A–5B or elastic sensor mesh 602 depicted in FIG. 6. Sensor 700 includes an RF transmitter/receiver 702 for transmitting signals to other sensors and for receiving signals from other sensors or from fixed RF sources, such as, for example, fixed RF sources 640–644 depicted in FIG. 6. Sensor 700 also includes a CPU 704 for executing instructions contained within system memory 708 for calculating the position of sensor 700 based on information received by RF transmitter/receiver 702. The position of sensor 700 is sent to a computer for display to a user and for manipulation, if desired, via I/O adapter 706. I/O adapter 706 may provide for a wired connection via, for example, a USB line, or may provide for wireless infrared (IR) or RF transmission to the computer.

In one embodiment of the present invention, an elastic sensor mesh is utilized to provide input to a computer for interpreting and/or translating American Sign Language (ASL). An elastic sensor mesh, such as described above, perhaps in the shape of a long-sleeved shirt with integrated gloves, is fitted to and worn by an ASL capable person. The elastic sensor mesh is connected to a computer, either by wire or wirelessly. As the person performs ASL, the position information of the arms, hands, and fingers of the ASL capable person is transmitted to the computer. The position information is then translated into movements by the computer. These movements are then translated by the computer, that has been trained to recognize the movements corresponding to ASL, into English, which may then be placed in the form of text or may be utilized by a speech synthesizer within or connected to the computer, such that persons unable to interpret ASL may, nevertheless communicate with the ASL capable person.

Although described with reference to American Sign Language and to English, the above described process may be applied to any type of language involving interpretation of movement rather than speech and may be translated into any language, such as, for example, German, French, or Japanese. Furthermore, the translation of physical movement is not limited to language, but may also be translated into musical tones, wherein different movements correspond to different tones or may be translated into media other than sound, such as light shows, laser show displays, or images on a video display wherein different movements produce differing visual effects.

Although the present invention has been described primarily with reference to determining a single static 3-dimensional shape of an object, the present invention may also be applied to determine the 3-dimensional motion of an object. In such case, the computer would make repeated measurements of the data received from the elastic sensor mesh, with each successive measurement separated from the previous by a small increment of time. Thus, a 3-dimensional image of the object may be created for each increment of time and merged to form a moving 3-dimensional image of the object.

It is important to note that while the present invention has been described in the context of a fully functioning data processing system, those of ordinary skill in the art will appreciate that the processes of the present invention are capable of being distributed in the form of a computer readable medium of instructions and a variety of forms and that the present invention applies equally regardless of the particular type of signal bearing media actually used to carry out the distribution. Examples of computer readable media include recordable-type media such a floppy disc, a hard disk drive, a RAM, and CD-ROMs and transmission-type media such as digital and analog communications links.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A method of translating physical movements into other media, the method comprising:

placing a plurality of sensors on an object;

each sensor of the plurality of sensors determining a corresponding position relative to at least one other sensor of said plurality of sensors;

receiving a first plurality of position data, wherein the first plurality of position data is based on a first set of positions of the plurality of sensors, and wherein the first plurality of position data corresponds to a first point in time;

determining a first shape of the object for the first point in time; and mapping the shape to an alternate media.

2. The method as recited in claim 1, wherein the alternate media is acoustical vibrations.

3. The method as recited in claim 2, wherein the acoustical vibrations produce speech.

4. The method as recited in claim 2, wherein the acoustical vibrations produce musical tones.

5. The method as recited in claim 1, wherein the alternate media is light.

6. The method as recited in claim 1, wherein the alternate media is a video display.

7. A computer program product in a computer readable medium, said computer program product for translating physical movements of an object into other media, wherein a mesh is disposed on the object, said mesh having a plurality of sensors distributed on nodes of the mesh, and wherein the computer program product comprises:

first instructions for a first sensor to emit a first radio-frequency signal and a second sensor to emit a second radio-frequency signal, wherein the first radio-frequency signal contains first identification information and the second radio-frequency signal contains second identification information, and wherein an initial distance between the first sensor and the second sensor is known;

second instructions for detecting the second signal with the first sensor;

third instructions for determining a change in position of the first sensor relative to a second position of the second sensor by using the second identification information, the strength of the second signal, and the initial distance between the first sensor and the second sensor;

fourth instructions for repeating the first instructions, the second instructions, and the third instructions for at least one other sensor of the plurality of sensors;

fifth instructions for determining a first plurality of position data regarding positions of at least two of the plurality of sensors, wherein the first plurality of position data corresponds to a first point in time;

sixth instructions for determining a first shape of the object for the first point in time using the first plurality of position data; and seventh instructions for mapping the first shape to an alternate media.

8. The computer program product as recited in claim 7, wherein the alternate media is acoustical vibrations.

9. The computer program product as recited in claim 8, wherein the acoustical vibrations produce speech.

10. The computer program product a recited in claim 8, wherein the acoustical vibrations produce musical tones.

11. The computer program product as recited in claim 7, wherein the alternate media is light.

12. The computer program product as recited in claim 7, wherein the alternate media is a video display.

13. The computer program product of claim 7 further comprising:

eight instruction, for determining a second plurality of position data regarding positions of at least two of the plurality of sensors, wherein the second plurality of position data corresponds to a second point in time;

ninth instructions for determining a second shape of the object for the second point in time using the second plurality of position data; and tenth instructions for mapping the second shape to an alternate media.

14. The computer program product of claim 13 further comprising:

eleventh instructions for correlating the first shape of the object and the second shape of the object to translate a change in shape of the object into physical movements of the object; and twelfth instructions for translating the physical movements of the object into American Sign Language; and translating the American Sign Language translated from the physical movements into a spoken language equivalent, wherein the alternate media is one of a text display of the spoken language equivalent and an audio output of the spoken language equivalent.

15. An apparatus for translating physical movements into other media, the method comprising:

a first sensor diseased on a first node of a mesh, a second sensor disposed on a second node of the mesh, and a third sensor disposed an a third node of the mesh, wherein a first initial distance between the first sensor and the second sensor is predetermined, a second initial distance between the second sensor and the third sensor is predetermined, wherein the mesh is adapted to be disposed on an object;

a first radio-frequency transmitter, a first radio-frequency receiver, and a first processor operably connected to the first sensor, said first processor containing first instructions to cause the first radio-frequency transmitter to emit a first identification signal;

a second radio-frequency transmitter, a second radio-frequency receiver, and a second processor operably connected to the second sensor, said second processor containing second instructions to cause the second radio-frequency transmitter to emit a second identification signal;

a third radio-frequency transmitter, a third radio-frequency receiver, and a third processor operably connected to the third sensor, said third processor containing third instructions to cause the third radio-frequency transmitter to emit a third identification signal;

wherein the first processor contains a fourth set of instructions to determine an identity of the second sensor using the second radio-frequency signal and a fifth set of instructions to determine a change in position of the first sensor relative to a position of the second sensor using the identity of the second sensor, a strength of the second identification signal, and the first initial distance;

means for determining a shape of the object at a first point in time based on the change in position of the first sensor when the mesh is disposed on the object; and means for mapping the shape to an alternate media.

16. The apparatus as recited in claim 15, wherein the alternate media is acoustical vibrations.

17. The apparatus as recited in claim 16, wherein the acoustical vibrations produce speech.

18. The apparatus as recited in claim 16, wherein the acoustical vibrations produce musical tones.

19. The apparatus as recited in claim 15, wherein the alternate media is light.

20. The apparatus as recited in claim 15, wherein the alternate media is a video display.

21. The apparatus as recited in claim 15, further comprising:

means for determining the shape of the object at a second point in time based on a second change in position of one of the first sensor, the second sensor, and the third sensor, when the mesh is disposed on the object; and means for translating a change in the shape of the object between the first point in time and the second point in time into physical movements;

means for translating the physical movements into American Sign Language; and means for translating the American Sign Language translated from the physical movements into a spoken language equivalent, wherein the alternate media is one of a text display of the spoken language equivalent and an audio output of the spoken language equivalent.

22. A method for translating physical movements into other media, the method comprising the steps of:

emitting a plurality of identification radio-frequency signals from a corresponding plurality of sensors, wherein each corresponding identification radio-frequency signal is adapted to uniquely identify a corresponding sensor in the plurality of sensors, and wherein each corresponding sensor further includes a processor adapted to determine an identity of at least one other sensor a the plurality of sensors based on a corresponding radio-frequency signal, emitted by the at least one other sensor, and wherein each corresponding processor is further adapted to determine a position of each corresponding sensor relative to at least one other sensor in the plurality of sensors based on the identity of the at least one other sensor, the strength of the corresponding identification radio-frequency signal of the at least one other sensor, and initial distances between each sensor in the plurality of sensors;

placing the plurality of sensors on an object;

determining a plurality of position data corresponding to a position of the object, said position data based on changes in positions of the plurality of sensors relative to the initial distances between each sensor in the plurality of sensors;

determining a shape of the object using the plurality of position data; and mapping the shape to an alternate media.

23. The method as recited in claim 22, wherein the plurality of sensors comprises an elastic sensor mesh.

24. An apparatus for translating physical movements into other media, comprising:

a plurality of sensors, wherein initial distances between each sensor of the plurality of sensors is known;

a corresponding plurality of transmitters operably connected to the plurality of sensors, wherein each transmitter is adapted to emit a radio-frequency signal;

a corresponding plurality of receivers operably connected to the plurality of sensors, wherein each receive is adapted to receive a radio-frequency signal;

a corresponding plurality of processors operably connected to the plurality of sensors, wherein each processor is adapted to cause a corresponding transmitter to transmit a corresponding identification signal that uniquely identifies a corresponding sensor, wherein each processor is further adapted to determine a corresponding identity of a corresponding sensor based on a corresponding identification signal, and wherein each processor is further adapted to determine changes in position of the corresponding sensors relative to at least one other sensor based on the identity of the at least one other sensor, the strength of the identification signal of the at least one other sensor, and the initial distance between a corresponding sensor and the at least one other sensor;

means for determining a plurality of position data of an object when the plurality of sensors are disposed on the object, wherein the plurality of position, data are based on changes in position of at least one of the plurality of sensors;

means for determining a shape of the object using the plurality of position data; and means for mapping the shape to an alternate media.

25. The apparatus as recited in claim 24, wherein the plurality of sensors comprises an elastic sensor mesh.

26. A method of translating physical movements into other media, the method comprising:

placing a mesh on an object, said mesh having a baseline shape and a plurality of nodes, wherein a plurality of sensors is distributed on the plurality of nodes, said plurality of sensors including a first sensor and a second sensor, and wherein an initial distance between the first sensor and the second sensor is predetermined;

emitting a first signal from the first sensor and a second signal from the second sensor, wherein the first signal and the second signal are radio frequency signals, and wherein the first signal contains first identification information and wherein the second signal contains second identification information;

detecting the second signal with the first sensor;

determining a change in position of the first sensor relative to a second position of the second sensor by using the second identification information, the strength of the second signal, and the initial distance between the first sensor and the second sensor;

for at least one other sensor in the plurality of sensors, repeating the emitting step, repeating the detecting step, and repeating the determining a change in position step;

determining a first plurality of position data regarding positions of at least two of the plurality of sensors, wherein the first plurality of position data corresponds to a first point in time, and wherein the first plurality of position data is determined by triangulation relative to the baseline shape of the mesh;

transferring the first plurality of position data through a central collection device;

transferring the first plurality of position data to an external processor;

determining, in the external processor, a first shape of the object for the first point in time using the first plurality of position data; and mapping the first shape to an alternate media.

27. The method of claim 26 further comprising:

determining a second plurality of position data regarding positions of at least two of the plurality of sensors, wherein the second plurality of position data corresponds to a second point in time, and wherein the second plurality of position data is determined by triangulation relative to the baseline shape of the mesh;

transferring the second plurality of position data through the central collection device;

transferring the second plurality of position data to the external processor;

determining a second shape of the object for the second point in time using the second plurality of position data; and mapping the second shape to an alternate media.

28. The method of claim 27 further comprising:

correlating the first shape of the object and the second shape of the object to translate a change in shape of the object into physical movements of the object;

translating the physical movements of the object into American Sign Language; and translating the American Sign Language translated from the physical movements into a spoken language equivalent, wherein the alternate media is one of a text display of the spoken language equivalent and an audio output of the spoken language equivalent.

* * * * *